United States Patent [19]

Raif

[11] 4,327,973

[45] May 4, 1982

[54] OPHTHALMOSCOPIC INSTRUMENT FOR MEASURING EYE DEFECTS

[75] Inventor: Joshua Raif, Kiryat Ono, Israel

[73] Assignee: Laser Industries, Ltd., Tel Aviv, Israel

[21] Appl. No.: 112,709

[22] Filed: Jan. 16, 1980

[30] Foreign Application Priority Data

Jan. 26, 1979 [IL] Israel ..................................... 56509

[51] Int. Cl.³ .............................................. A61B 3/10
[52] U.S. Cl. ........................................... 351/9; 351/16
[58] Field of Search .................................. 351/9, 6, 16

[56] References Cited

FOREIGN PATENT DOCUMENTS 2825885  1/1979  Fed. Rep. of Germany .......... 351/9

*Primary Examiner*—John K. Corbin
*Assistant Examiner*—Rodney B. Bovernick

*Attorney, Agent, or Firm*—Benjamin J. Barish

[57] ABSTRACT

An ophthalmoscopic instrument for measuring eye defects, particularly cataract and flare, is described including a beam-splitter for splitting a light-beam into a first portion travelling through a first path to the examined eye from which it is reflected back to a viewing station, and a second portion travelling through a second path to a light scatterer from which it is reflected back to the viewing station. A variable filter is provided in the second path and is varied to match the intensity of the light arriving at the viewing station from the second path with the light arriving at the viewing station from the first path, to provide an indication of the intensity of the later light. The instrument further includes a second filter which is selectively either introduced into the second path to adapt the instrument for measuring flare, or removed from the second path to adapt the instrument for measuring cataract.

12 Claims, 7 Drawing Figures

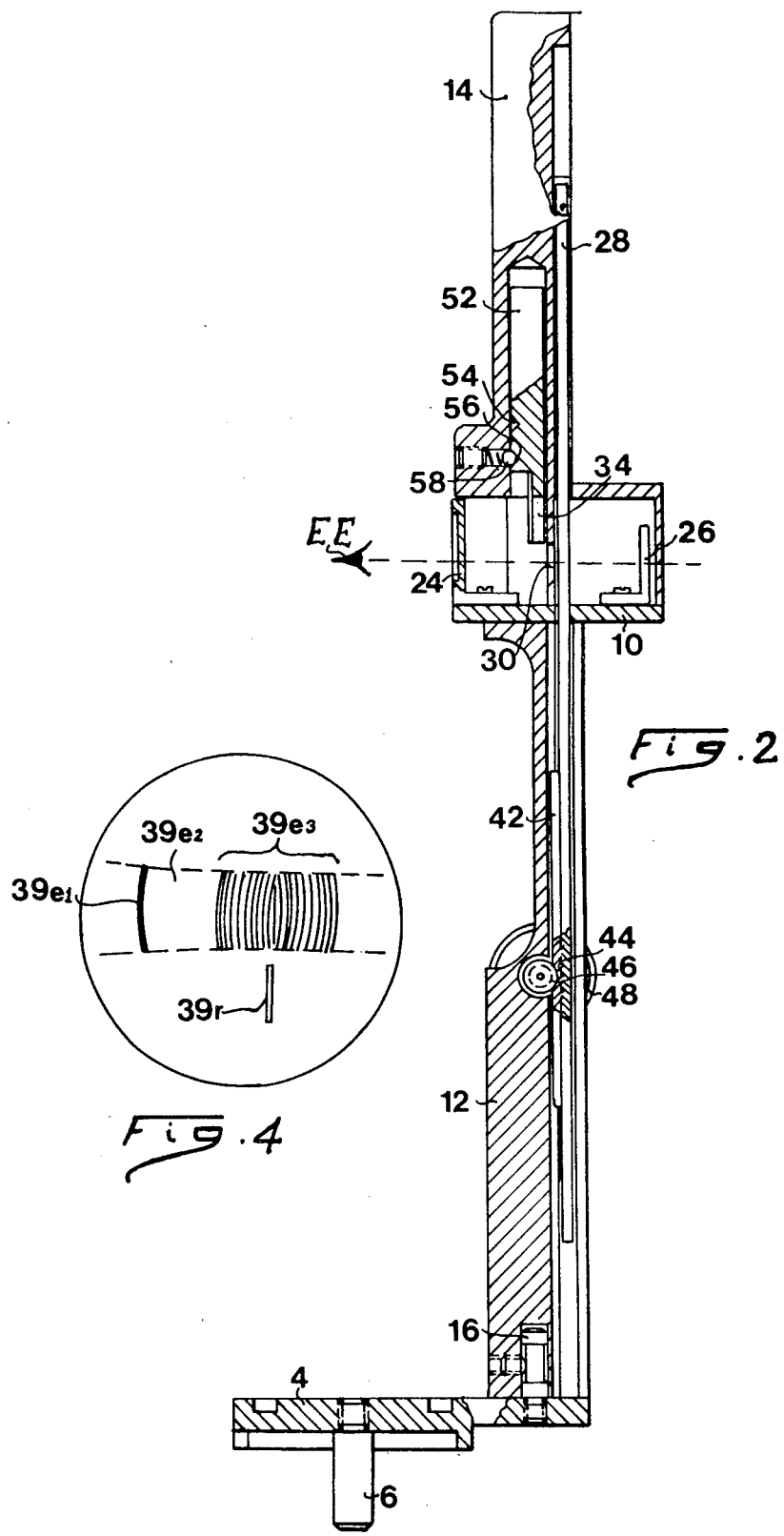

OPHTHALMOSCOPIC INSTRUMENT FOR MEASURING EYE DEFECTS

The present invention relates to ophthalmoscopic instruments for measuring eye defects. The invention is particularly directed to improvements in the instrument described in "Archives of Ophthalmology," by Blumenthal, 1977, Vol. 95, pg. 323, and in Israel Pat. No. 46356 filed Dec. 7, 1974.

The above patent describes an ophthalmoscopic instrument for measuring defects in an examined eye including means for splitting a light beam from an external source into a first portion travelling through a first path to the examined eye from which it is reflected back to a viewing station, and a second portion travelling through a second path to a light scatterer from which it is reflected back to the viewing stations; a variable filter in the second path; and means for varying the filter in order to match the intensity of the light arriving at the viewing station from the second path with the light arriving at the viewing station from the first path to provide an indication of the intensity of the light arriving at the viewing station from the first path. The intensity of this light arriving at the viewing station provides an indication of the health condition of the eye; that is, the healthier is the eye, the more transparent it is, and therefore the less will be the amount of light reflected back to the examiner.

The present invention is particularly directed to a number of improvements in the device disclosed in that patent. These improvements will probably be better understood by first briefly describing the two eye defects of cataract and flare.

Thus, cataract is an opacity in the eye lens, whereas flare is a similar opacity but in the anterior chamber between the cornea and the eye lens. When the examined eye is free of both cataract and flare, the eye lens and the anterior chamber are both substantially transparent, and therefore a beam of light projected into the eye will produce relatively little reflection back out through the eye. However, if the patient is suffering from either cataract or flare, the opacity of the eye will cause a substantial amount of the light projected into the eye to be reflected back out of the eye. The traditional method of examination for both conditions is to project a beam of light into the eye by the use of a slit lamp and to discern, by visual observation, how much light is reflected back out of the eye: a small amount of reflection indicates a healthy eye, and a relatively large amount of reflection indicates cataract and/or flare.

The above-described instrument provides a more objective (when compared to the traditional) method of measuring the quantity of light reflected back out through the eye, and thereby a more objective index of the condition of the eye. However, this instrument actually measures only one condition, either cataract or flare, depending on the properties of the variable filter. Since in the flare condition, the opacity appears in the anterior chamber between the cornea and the lens, it produces a lower intensity of reflections than the cataract condition, and therefore if the instrument (particularly the filter) of the above-cited patent is designed for examining for one condition, it would not be usable for satisfactorily examining for the other condition.

The present invention is directed to a number of improvements in that instrument, including the following:

According to one important improvement, the instrument further includes a second filter; and means selectively for introducing the second filter into the second path to adapt the instrument for measuring the eye defect of flare, or for removing same from the second path to adapt the instrument for measuring the eye defect of cataract.

By thus providing the second filter which may be selectively introduced or removed with respect to the second light path (i.e., the reference intensity path including the light scatterer), the first (variable) filter may be designed for optimum optical characteristics when used alone to examine for cataract, and the second selectively removable filter may be designed for optimum optical characteristics to examine for flare when it is included in the optical path with the first (variable) filter.

Two preferred embodiments of the invention are described below wherein the means for splitting the light beam comprises a first beam-splitter at the upstream side of the light scatterer, the instrument including a second beam-splitter at the downstream side of the light scatterer between the two filters and the viewing station for reflecting thereto light from the light scatterer exiting from the filters and for transmitting to the viewing station reflected from the examined eye.

In one described embodiment, both the beam-splitters are disposed in a vertical side-by-side relationship at the front end of the instrument when the instrument is in its operative position facing the examined eye, the two beam-splitters being separated by a light-absorbing baffle, the light scatterer being disposed at the rear end of the instrument in an intermediate position between the two beam-splitters to receive said second portion of the light beam unhindered by said light-absorbing baffle.

In the second described embodiment of the invention, when the instrument is in operative position facing the examined eye, the two beam-splitters are disposed in an inclined relationship facing the light scatterer which is vertically spaced from the two beam-splitters in position to receive light from the first beam-splitter and to reflect it back to the second beam-splitter. This arrangement enables the instrument to be constructed more compactly and therefore with less possibility of nose interference particularly when examining the left eye.

According to a further feature, it has been found that improved results can be obtained by including an optical aperture in the second path between the light scatterer and the second beam-splitter.

Further features and advantages of the invention will be apparent from the description below.

The invention is herein described, by way of example only, with reference to the accompanying drawings, wherein:

FIG. 2 is a side sectional view, along lines II—II of FIG. 1;

FIG. 4 illustrates the light spots as seen by the examiner at the viewing station;

Figure 1:
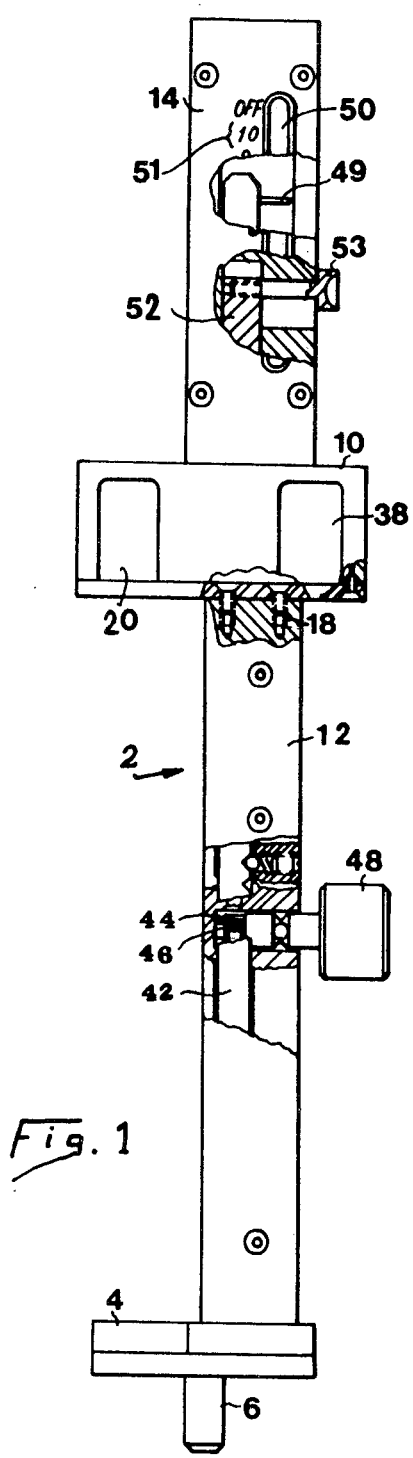
FIG. 1 is a rear view (i.e., from the examiner's side) of one form of instrument constructed in accordance with the invention.
Figure 3:
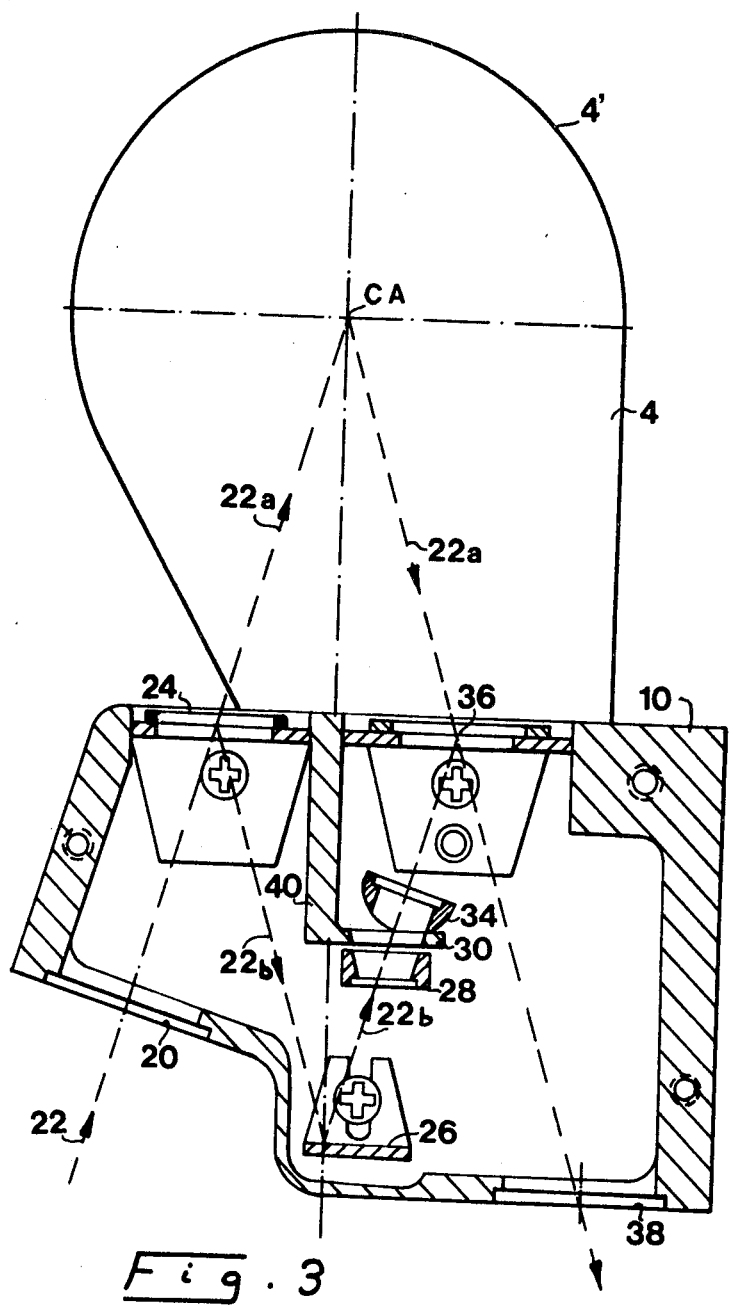
FIG. 3 is a top sectional view, along lines III—III of FIG. 1.

The instrument illustrated in FIGS. 1–3 of the drawings comprises a housing, generally designated 2, fixed to a plate 4 adapted to be mounted to a conventional slit-lamp (not shown) by means of a pin 6. FIG. 3 illustrates the configuration of the mounting plate 4 in plan view, wherein it will be seen that its outer extremity 4' at the opposite end to which housing 2 is secured, is of semi-circular shape and has a center axis CA which defines the position of the examined eye EE (FIG. 2) when the instrument is in use.

Housing 2 includes a main section 10 containing the main optical elements of the instrument with which the examined eye EE is to be aligned. The housing 2 further includes a lower housing section 12 and an upper housing section 14, the lower housing section 12 being attached to the mounting plate 4 by means of a fastener 16 (FIG. 2) and to the main housing section by fasteners 18 (FIG. 1).

The main housing section 10 is formed at its rear side (i.e., the side facing the examiner) with an entrance window 20 receiving the beam of light, indicated by arrow 22, from the slit-lamp (not shown). This beam of light is directed through window 20 so as to intersect the center axis CA of the mounting plate 4, and to enter the examined eye EE to be positioned at that center axis.

A beam-splitter 24 at the opposite side of housing 10 (namely that side facing the examined eye EE of the patient) splits the light beam 22 into two portions, namely: a first portion 22a, which is transmitted by the beam-splitter to continue along the same path, this constituting a first path 22a, to the examined eye EE at the center axis CA; and a second portion, which is reflected by the beam-splitter along a second path 22b back into housing section 10 where it impinges a light scatterer 26 at the rear end of the housing section.

Light scatterer 26 is formed with a scattering surface which reflects the light substantially uniformly in all directions. The portion of the light continuing in the second path 22b passes through a variable density filter 28, an optical aperture 30, and a two-position filter 34 before it is intercepted by a second beam-splitter 36, which reflects the light back to an exit window 38 at the rear side of housing section 10.

The second beam-splitter 36 also receives the light reflected by the examined eye EE travelling along path 22a, and passes same to the exit window 38 at the rear side of the instrument.

In practice, the examiner views both portions of the light beam via a microscope (not shown) aligned with the exit window 22 at the rear side of the instrument housing section 10. The field of view as seen under the microscope is shown at 39 in FIG. 4, wherein 39e (i.e. $39e_1$–$39e_3$) indicates the shape of the light spots reflected from the eye (via path 22a), and 39r indicates the shape of the light spot as reflected from the light scatterer 26 (via path 22b). These light spots are described more particularly below.

Housing section 10 further includes a light absorbing baffle 40 separating the two beam splitters 24 and 36 but permitting the light from beam splitter 24 to pass via path 22b unhindered to the light scatterer 26. The two filters 28 and 30 are thus shielded by baffle 40 from the light from the first beam-splitter 24 except that reflected back via path 22b to the light scatterer 26 which reflects same through the two filters and the optical aperture 30 to the second beam-splitter 36.

Variable filter 28 is a linearly-movable, variable-density type. It includes a holder 42 (FIG. 2) extending into the lower housing section 12 and formed with teeth 44 meshing with the teeth of a gear 46 carried at the end of a rotatable knob 48. It will be seen that by rotating knob 48, the variable filter holder 42 may be moved upwardly or downwardly to position different portions of the filter, having different optical densities, in alignment with the optical aperture 30. The filter holder 42 carries an index marker 49 at its upper end which is viewable through a window 50 in the upper housing section 14. The position of the filter index 49, and thereby the condition of the eye, is indicated by graduation markings 51 along the edge of the window 50.

As also shown in FIG. 2, the two-position filter 34 is carried in a holder 52 disposed within the upper housing section 14. It is movable to either of its two positions by manipulating a thumb knob 53 (FIG. 1) attached to the filter holder 52 and projecting through a slot in the upper housing section. The two positions are defined by two notches 54, 56 formed at the lower end of holder 52 and adapted to receive a spring-urged ball 58 carried by the housing. The ball 58 and the notches 54, 56 thus serve as ball-and-detent means for releasably retaining filter holder 52 in either of its two positions. The filter 34 is carried at the lower end of holder 52, at the patient's side of the optical aperture 30, such that when the holder 52 is in its upper position (as illustrated in FIG. 2), filter 34 is supported above the optical aperture 30 so as not to intercept the light passing through path 22b; whereas when the holder 52 is in its lower position, filter 34 is aligned with the optical aperture 30 so as to intercept the light passing through path 22b.

The instrument illustrated in FIGS. 1–3 is used in the following manner.

First, the instrument is attached to the slit-lamp (not shown) by means of pin 6 carried by the mounting plate 4 with the two beam-splitters 24, 36 facing the patient whose eye EE is to be examined. The instrument is oriented such that the light from the slit-lamp passes through the entrance window 20 along line 22 to intercept the center axis CA of the mounting plate 4. The patient then positions his head with the eye EE to be examined located precisely in alignment with the central axis CA of the mounting plate 4 so as to intercept the light beam inletted from the slit-lamp along path 22.

Next, the examiner determines whether the examination is to be for cataract or flare. If the examination is to be for flare, he moves the thumb-knob 53 downwardly which introduces the two-position filter 34 into alignment with the optical aperture 30 (FIG. 2); and if the examination is to be for cataract, he raises the thumb-knob to lift the variable filter 34 out of alignment with the optical aperture, i.e., to the position illustrated in FIG. 2.

It will be seen that the inletted beam 22 is first intercepted by beam-splitter 24, which permits a portion of the beam to pass therethrough along path 22a and reflects another portion of the beam to a second path 22b.

The portion of the light beam travelling through path 22a enters the examined eye EE at the central axis CA which eye then reflects the beam back to beam-splitter 36. The latter permits the beam to pass to the exit window 38 for viewing by the examiner through the microscope (not shown).

The portion of the light beam reflected by beam-splitter 24 to path to 22b is intercepted by the light scatterer 26 and is reflected through the variable density filter 28, optical aperture 30, and two-position filter 34 before impinging on beam-splitter 36, which reflects it to the exit window 38 for viewing by the examiner through the microscope (not shown).

FIG. 4 illustrates the various spots of light appearing at the viewing station as seen by the examiner through the microscope. Light spot $39r$ is that passing through path $22b$ from the light scatterer 26, which path includes the two filters 28, 34 and the optical aperture 30. The light passing via path $22a$ from the examined eye appears in three distinct regions, namely: region $39e_1$ which is the corneal reflection, usually very intense; region $39e_2$, which is the anterior chamber scattering; and region $39e_3$ which is the eye lens scattering. When examining for flare, the reference spot $39r$ is matched with region $39e_2$ and when examining for cataract, it is matched with region $39e_3$. The examiner aligns the reference spot $37r$ with the selected region by adjusting the slit lamp itself.

As the examiner views the reference spots $39r$ with the appropriate region ($39e_2$ for flare, or $39e_3$ for cataract), he effects the matching by rotating knob 48 to move the variable filter 28, and then raises his eyes slightly to see the position of the index marker 49 with respect to the graduation markings 51. This indication of the position of the variable filter provides an indication of the intensity of the light reflected from the examined eye, and thereby an index of the health condition of the examined eye.

If the examination was made with the two-position filter 34 in its lower position (i.e. aligned with the optical aperture 30), then the index indicates the degree of flare of the examined eye; and if it was made with the two-position filter 34 in its raised position (i.e., out of alignment with the optical aperture 30 as shown in FIG. 2), then the index indicates the degree of cataract of the examined eye.

By thus providing the two-position filter 34, which may be selectively introduced or removed during the examination procedure, the same instrument may be used for examination for both cataract and flare.

Figure 5:
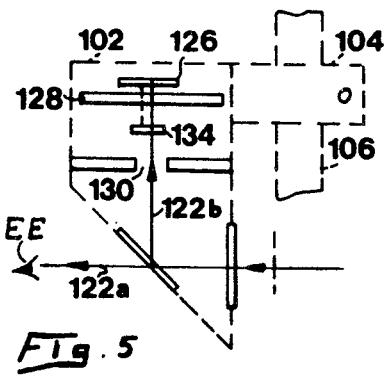
FIG. 5 is a rear diagrammatic view of a second form of instrument in accordance with the invention.
Figure 6:
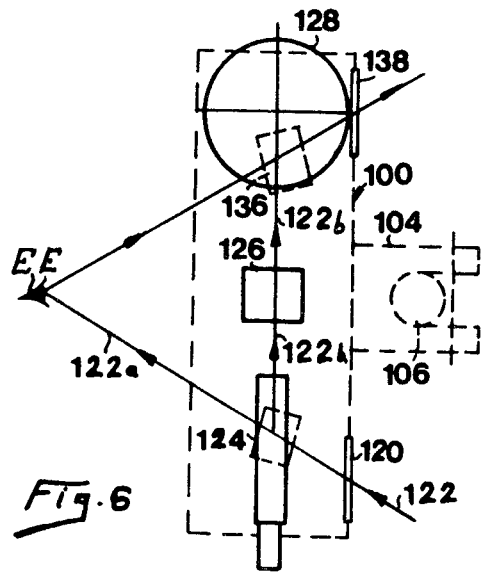
FIG. 6 is a diagrammatic side view of the instrument of FIG. 5.
Figure 7:
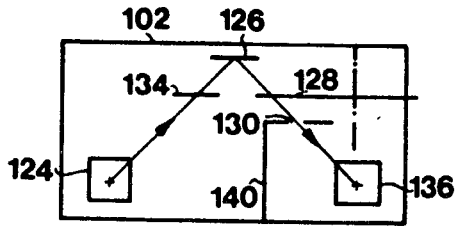
FIG. 7 is a diagrammatic top view of the instrument of FIG. 5.

A second embodiment of the invention is diagramatically illustrated in FIGS. 5-7. This embodiment enables the instrument to take a more compact construction, thereby reducing the possibility of nose interference and enabling the use of a more simplified mechanical arrangement.

The instrument illustrated in FIGS. 5-7 includes a housing 102 carried by a mounting plate 104 also adapted to be attached to the conventional slit-lamp (not shown), in this case to the tonometer rod 106 of the slit-lamp. The housing 102 includes an entrance window 120 adapted to receive the beam of light from the slit-lamp travelling along path 122 in alignment with the examined eye EE. This beam of light is intercepted by beam-splitter 124 which permits a portion of the beam to travel along path $122a$ to the examined eye EE, and reflects another portion to travel along path $122b$ to a light scatterer 126, which latter reflects the light to a second beam-splitter 136. Beam-splitter 136 receives, via path $122a$, the light reflected from the examined eye EE and passes same to an exit window 138. It also receives, via path $122b$, the light from light scatterer 126 and reflects same through the same exit window 138, path $22a$ including a variable filter 128, an optical aperture 130, and a two-position filter 134. A light-absorbing baffle 140 (FIG. 7) separates the two beam-splitters, this baffle including an opening which constitutes the optical aperture 130.

Variable filter 128 corresponds to filter 28 in the FIGS. 1-3 embodiment, except that filter 128 is of the rotatable type, rather than of the linear type described above. Optical aperture 130 corresponds to optical aperture 30 in FIGS. 1-3 except that it is formed in the baffle 140. The two-position filter 134 corresponds to filter 34 in the FIGS. 1-3 embodiment, except that it is on the upstream side of the light scatterer. However, like filter 34, filter 134 is also selectively positionable into alignment with the optical aperture 130 for examining for flare, or out of alignment with the optical aperture for examining for cataract.

Thus, the instrument illustrated in FIGS. 5-7 includes the same essential elements and is used in the same manner, as described above with respect to the instrument illustrated in FIGS. 1-3. However, instead of having the beam-splitters in a side-by-side relationship facing the examined eye, with the light scatterer disposed at the rear end of the instrument at an intermediate position between the two beam-splitters as described with respect to the FIGS. 1-3, the embodiment illustrated in FIGS. 5-7 provides the two beam-splitters in an inclined relationship, with the light scatterer disposed vertically spaced from them in position to receive light from the first beam-splitter and to reflect it back to the second beam-splitter. In addition the instrument of FIGS. 5-7 includes a rotatably variable filter 128, rather than a linearly variable one (28) as in FIGS. 1-3. The foregoing arrangement in FIGS. 5-7 enables the instrument to take a much more compact construction, thereby reducing the possibility of nose interference during the examination and also simplifying the mechanism needed to be used.

While the invention has been described with respect to two preferred embodiments, it will be appreciated that many variations, modifications and other applications of the invention may be made.

I claim:

1. An ophthalmoscopic instrument for measuring defects in an examined eye including means for splitting a light beam from an external source into a first portion travelling through a first path to the examined eye from which it is reflected back to a viewing station, and a second portion travelling through a second path to a light scatterer from which it is reflected back to the viewing station; a variable filter in the second path; and means for varying the filter in order to match the intensity of the light arriving at the viewing station from the second path with the light arriving at the viewing station from the first path to provide an indication of the intensity of the light arriving at the viewing station from the first path; characterized in that the instrument further includes a second filter; and means selectively for introducing the second filter into the second path to adapt the instrument for measuring the eye defect of flare, or for removing same from the second path to adapt the instrument for measuring the eye defect of cataract.

2. An instrument according to claim 1, wherein said means for splitting the light beam comprises a first beam-splitter at the upstream side of the light scatterer, the instrument including a second beam-splitter at the downstream side of the light scatterer between the two filters and the viewing station for reflecting thereto light from the light scatterer exiting from the filters and for transmitting to the viewing station reflected from the examined eye.

3. An instrument according to claim 2, wherein both said beam-splitters are disposed in a vertical side-by-side relationship at the front end of the instrument when the instrument is in its operative position facing the examined eye, the two beam-splitters being separated by a light-absorbing baffle, the light scatterer being disposed at the rear end of the instrument in an intermediate position between the two beam-splitters to receive said second portion of the light beam unhindered by said light-absorbing baffle.

4. An instrument according to claim 3, wherein both the filters are disposed in the second path between the light scatterer and the second beam-splitter in position such as to be shielded by the light-absorbing baffle of direct light from the first beam-splitter but to receive, and to transmit therethrough to the second beam-splitter, only the light reflected from the light scatterer.

5. An instrument according to claim 4, further including an optical aperture in said second path between the light scatterer and the second beam-splitter.

6. An instrument according to claim 2, wherein said variable filter is linearly movable within a housing having an opening at one end just above the viewing station, the housing further including graduation markings adjacent to said opening, the variable filter carrying an index marking viewable through the housing opening adjacent to the graduation markings to provide an indication of the position of the variable filter and thereby an index of the condition of the examined eye.

7. An instrument according to claim 2, wherein, when the instrument is in operative position facing the examined eye, the two beam-splitters are disposed in an inclined relationship facing the light scatterer which is vertically spaced from the two beam-splitters in position to receive light from the first beam-splitter and to reflect it back to the second beam-splitter.

8. An instrument according to claim 7 further including a light-absorbing baffle between the two beam-splitters, which baffle includes a passageway for conducting the second portion of light from the light scatterer through the two filters to the second beam-splitter.

9. An instrument according to claim 1, wherein the second filter is carried by a holder movable to either of two positions, the instrument including ball-and-detent means for retaining said holder in either of its two positions.

10. An instrument according to claim 9, wherein said holder further includes a thumb-knob manipulatable by the examiner for selectively moving the holder to either of its two positions.

11. An instrument according to claim 1, wherein said variable filter is a rotatable one.

12. An instrument according to claim 11, wherein said second filter is a linearly movable one.

* * * * *